(12) United States Patent
Mallard

(10) Patent No.: US 10,744,147 B2
(45) Date of Patent: Aug. 18, 2020

(54) COMPOSITION COMPRISING AVERMECTIN COMPOUNDS WITHOUT SOLID FATTY SUBSTANCES

(71) Applicant: Nestlé Skin Health SA, Lausanne (CH)

(72) Inventor: Claire Mallard, Mougins (FR)

(73) Assignee: NESTLÉ SKIN HEALTH S.A., Lausanne (CH)

(*) Notice: Subject to any disclaimer, the term of this patent is extended or adjusted under 35 U.S.C. 154(b) by 0 days.

(21) Appl. No.: 16/463,810

(22) PCT Filed: Nov. 23, 2017

(86) PCT No.: PCT/EP2017/080146
§ 371 (c)(1),
(2) Date: May 23, 2019

(87) PCT Pub. No.: WO2018/096008
PCT Pub. Date: May 31, 2018

(65) Prior Publication Data
US 2019/0275069 A1    Sep. 12, 2019

(30) Foreign Application Priority Data
Nov. 24, 2016  (EP) .................................. 16306555

(51) Int. Cl.
| A61K 9/00 | (2006.01) |
| A61K 31/7048 | (2006.01) |
| A61K 9/107 | (2006.01) |
| A61K 9/06 | (2006.01) |
| A61K 9/10 | (2006.01) |

(52) U.S. Cl.
CPC ........ *A61K 31/7048* (2013.01); *A61K 9/0014* (2013.01); *A61K 9/06* (2013.01); *A61K 9/10* (2013.01); *A61K 9/107* (2013.01)

(58) Field of Classification Search
None
See application file for complete search history.

(56) References Cited

U.S. PATENT DOCUMENTS

| 5,773,422 A | 6/1998 | Komer |
| 2005/0143325 A1 | 6/2005 | Guzzo et al. |
| 2006/0100165 A1 | 5/2006 | Manetta et al. |
| 2007/0116731 A1* | 5/2007 | Astruc ................. A61K 9/0014 424/401 |
| 2008/0214657 A1 | 9/2008 | Spring et al. |
| 2009/0035338 A1* | 2/2009 | Segura-Orsoni ..... A61K 9/0014 424/401 |
| 2009/0233877 A1 | 9/2009 | Kaoukhov et al. |
| 2009/0264378 A1 | 10/2009 | Kaoukhov et al. |
| 2010/0093652 A1 | 4/2010 | Spring et al. |
| 2012/0004200 A1 | 1/2012 | Nadau-Fourcade et al. |
| 2013/0108563 A1 | 5/2013 | Diaz-Astruc et al. |
| 2015/0105340 A1 | 4/2015 | Spring et al. |
| 2016/0303152 A1 | 10/2016 | Nayar |
| 2016/0303154 A1 | 10/2016 | Nayar |
| 2016/0303155 A1 | 10/2016 | Nayar |

FOREIGN PATENT DOCUMENTS

| CN | 101773470 | 7/2010 |
| FR | 2924944 A1 | 6/2009 |
| WO | WO-2016/022066 A1 | 2/2016 |
| WO | WO-2016/024855 A1 | 2/2016 |

OTHER PUBLICATIONS

International Search Report issued in PCT/EP2017/080146 and dated Jan. 30, 2018.
International Search Report issued in PCT/EP2017/080147 and dated Jan. 24, 2018.
International Search Report issued in PCT/EP2017/080148 and dated Feb. 6, 2018.
Communication pursuant to Article 94(3) EPC dated Mar. 23, 2020 issued in corresponding European Application No. 16306554.3 (4 pages).

* cited by examiner

Primary Examiner — Robert A Wax
Assistant Examiner — Melissa S Mercier
(74) Attorney, Agent, or Firm — Foley & Lardner LLP; Sunit Talapatra

(57) ABSTRACT

Composition comprising avermectin compounds without solid fatty substances The invention relates to a dermatological or pharmaceutical composition comprising at least one aqueous phase and at least one active phase comprising at least one active compound chosen from avermectin compounds and at least one solvent and/or propenetrating agent of avermectin compounds, where the composition comprises less than 3% by weight of solid fatty substances at room temperature and at atmospheric pressure, relative to the total weight of the composition. The invention relates also to the composition for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea. Finally, the invention relates to a method for preparing the composition.

22 Claims, No Drawings

COMPOSITION COMPRISING AVERMECTIN COMPOUNDS WITHOUT SOLID FATTY SUBSTANCES

CROSS-REFERENCE TO RELATED APPLICATIONS

This application is a National Phase of International Patent Application No. PCT/EP2017/080146, filed Nov. 23, 2017, published on May 31, 2018 as WO 2018/096008 A1, which claims priority to European Patent Application No. 16306555.0, filed Nov. 24, 2016. The contents of these applications are herein incorporated by reference in their entirety.

The invention relates to a dermatological or pharmaceutical composition comprising at least one active compound chosen from avermectin compounds with less than 3% by weight of solid fatty substances at room temperature and at atmospheric pressure.

In particular, the invention relates to a dermatological or pharmaceutical composition comprising at least one aqueous phase and at least one active phase comprising at least one active compound chosen from avermectin compounds and at least one solvent and/or propenetrating agent of avermectin compounds, where the composition comprises less than 3% by weight of solid fatty substances at room temperature and at atmospheric pressure, relative to the total weight of the composition.

The invention relates also to the composition for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea.

Finally, the invention relates to a method for preparing the composition.

The class of avermectins, a group of macrocyclic lactones produced by the bacterium *Streptomyces avermitilis* (Reynolds J E F (Ed) (1993) Martindale, The extra pharmacopoeia, 29$^{th}$ Edition, Pharmaceutical Press, London), namely includes ivermectin, invermectin, avermectin, abamectin, doramectin, eprinomectin, and selamectin.

In particular, ivermectin is a mixture of two compounds, 5-O-demethyl-22,23-dihydroavermectin $A_{1a}$ and 5-O-demethyl-22-23-dihydroavermectin $A_{1b}$.

In the middle of the 1980s, ivermectin was presented as a broad-spectrum anti-parasitic medicinal product for veterinary use (W. C. CAMPBELL, et al., (1983) "Ivermectin: a potent new anti-parasitic agent", Science, 221, 823-828). It is effective against most common intestinal worms (except tapeworms), most acarids and some lice. It in particular exhibits considerable affinity for the glutamate-dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand-dependent chloride channels, such as those involving the neuromediator GABA (gamma-aminobutyric acid).

Ivermectin is more particularly an anthelmintic. It has been administered in humans in the treatment of onchocerciasis caused by *Onchocerca volvulus*, of gastrointestinal strongyloidias (anguillulosis) and of human scabies and also in the treatment of microfilaremia diagnosed or suspected in individuals suffering from lymphatic filariosis due to *Wuchereria bancrofti*.

More recently, compounds of avermectin family have been used in the treatment of dermatological conditions such as rosacea in a topical pharmaceutical composition suited for human administration.

For example, the document US 2006/0100165 describes the use of topical compositions comprising ivermectin for the treatment of dermatological conditions such as rosacea which are in addition chemically and physically stable over time.

Nevertheless, these compositions are in the form of a cream with a high viscosity usually ranging from 40 Pa·s to 90 Pa·s, and therefore are not pourable which limits their ability to be sprayable using either a mechanic pump spray or a pressurized spray.

There is therefore a need to manufacture compositions comprising avermectin compounds, especially ivermectin, which are pourable and sprayable without impeding on their chemical and physical stability over time.

As per CDER (Center for Drug Evaluation and Research) data standards manual definitions for topical dosage forms, a liquid is pourable if it flows and conforms to its container at room temperature. It displays Newtonian or pseudoplastic flow behavior. A semisolid is not pourable if it does not flow or conform to its container at room temperature. It does not flow at low shear stress and generally exhibits plastic flow behavior.

It has now been found, surprisingly, that a dermatological or pharmaceutical composition comprising at least one active compound chosen from avermectin compounds where the composition comprises less than 3% by weight of solid fatty substances at room temperature and at atmospheric pressure, relative to the total weight of the composition, is pourable while having good chemical and physical stability over time.

The present invention thus concerns a dermatological or pharmaceutical composition comprising at least one aqueous phase and at least one active phase comprising at least one active compound chosen from avermectin compounds and at least one solvent and/or propenetrating agent of avermectin compounds, where the composition comprises less than 3% by weight of solid fatty substances at room temperature and at atmospheric pressure, relative to the total weight of the composition.

The composition according to the invention has a viscosity ranging from 1000 to 10000 cP, in particular ranging from 1000 to 5000 cP measured at room temperature using a Brookfield LV and therefore is pourable.

In addition, the composition according to the invention has a yield stress ranging from 5 Pa to 50 Pa, preferably from 10 to 20 Pa at room temperature using a Malvern rheometer.

Hence, the composition according to the invention is sprayable using either a mechanic pump spray or a pressurized spray making its application easier on the skin.

Moreover, the texture of the composition is light.

In addition, the composition according to the invention exhibits good chemical and physical stability over time, even at a temperature above ambient temperature (for example, 40° C.).

"Chemical stability" means that the amount of avermectin compounds of the composition does not change more than 5% by weight relative to the initial amount in avermectin compounds of the composition.

"Physical stability" means that the composition meets the acceptance criteria for appearance, physical attributes and functionality test (e.g. color, phase separation, dose delivery per actuation). More precisely, the physical stability means that at least two of the following criteria, preferably all of the following criteria: microscopic aspect, macroscopic aspect, viscosity and pH, do not significantly vary after manufacture time during 1 month, preferably during 2 months and even more preferably during 3 months.

Thus, the composition of the present invention is in the form of a pourable fluid emulsion wherein the active compound is fully solubilized in the composition while remaining chemically and physically stable over time, especially without formation of crystals.

The present invention also concerns the dermatological or pharmaceutical composition as defined above for use in the treatment of rosacea, of common acne, of seborrheic dermatitis, of perioral dermatitis, of acneiform rashes, of transient acantholytic dermatosis, of acne necrotica miliaris and of atopic dermatitis, and preferably for use in the treatment of rosacea.

The invention concerns also a method for preparing the composition comprising the following steps:

a) mixing avermectin compounds with the other components of the active phase b) mixing the constituents of the aqueous phase to homogeneity, then c) incorporating the active phase into the aqueous phase so as to form the composition.

According to the present invention, "active phase" refers to the phase comprising the active compound.

In particular, during the preparation of the composition of the present invention, it has been observed that the avermectin compounds have been solubilized in the active phase despite of the fact that the said active phase comprises a low amount of solid fatty substances.

Hence, the avermectin compounds are solubilized into the final composition thanks to their solubilization into the active phase.

Indeed, the only know way to solubilize ivermectin is thanks to a fatty phase comprising fatty compounds. In particular, ivermectin is solubilized and stabilized in the fatty drops of the emulsion.

Consequently, it is surprising, in the context of the invention, that ivermectin is solubilized and stable in the present composition which does not comprise or very few solid fatty substances.

Other subject-matters, characteristics, aspects and advantages of the invention will become even more clearly apparent on reading the description and the examples which follow.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

As described above, the composition according to the invention comprises less than 3% by weight of solid fatty substances at room temperature and at atmospheric pressure, relative to the total weight of the composition.

"Solid fatty substance" means a compound which is solid at room temperature and at atmospheric pressure and insoluble in water, that is to say a solubility at room temperature and at atmospheric pressure of less than or equal to 1% by weight relative to water.

Preferably, the solid fatty substances are chosen from fatty acids, fatty alcohols, waxes, gums, and mixtures thereof.

As fatty acid, mention may be made of linoleic acid, stearic acid.

As a fatty alcohol, mention may be made of stearyl alcohol, cetostearyl alcohol and cetyl alcohol.

As wax, mention may be made of beeswax, carnauba wax, paraffin wax and candelilla wax.

As gum, mention may be made of silicone gums.

In a preferred embodiment, the composition does not comprise stearyl alcohol and cetyl alcohol.

The dermatological or pharmaceutical composition according to the invention comprises less than 3% by weight, preferably, less than 2.5% by weight of solid fatty substances at room temperature and at atmospheric pressure, relative to the total weight of the composition.

In a particular embodiment of the invention, the dermatological or pharmaceutical composition does not comprise solid fatty substances at room temperature and at atmospheric pressure.

In a preferred embodiment of the invention, the dermatological or pharmaceutical composition comprises less than 4% by weight, preferably less than 3% by weight of liquid fatty substances at room temperature and at atmospheric pressure, relative to the total weight of the composition.

"Liquid fatty substance" means a compound which is liquid at room temperature and at atmospheric pressure and insoluble in water, that is to say a solubility at room temperature and at atmospheric pressure of less than or equal to 1% by weight relative to water.

The avermectin compounds that are used according to the invention are preferably chosen from ivermectin, invermectin, avermectin, abamectin, doramectin, eprinomectin and selamectin.

Preferably, the avermectin compound is ivermectin.

The composition according to the invention comprises preferably from 0.01 to 10% by weight, more preferably from 0.1 to 5% by weight of avermectin compounds, relative to the total weight of the composition.

The dermatological or pharmaceutical composition according to the invention comprises at least one solvent and/or propenetrating agents of avermectin compounds.

A solvent of avermectin compounds is defined as a liquid compound in which the compounds of the avermectin family, in particular ivermectin, have a solubility at room temperature and at atmospheric pressure of more than or equal to 2% by weight relative to the composition comprising only said solvent or said solvent in association with one or more solvents of avermectin compounds.

Solubility of a compound into one or more solvents is defined as the amount of compound that passes into a solution constituted of the one or more solvents to achieve a saturated solution at constant temperature and pressure (stirring of the saturated solution from 16 to 24 hours). Solubility is expressed in terms of maximum volume or mass of the compound that dissolves in a given volume or mass of one or more solvents.

A propenetrating agent of avermectin compounds makes it possible to facilitate the penetration of the compounds of the avermectin family into the skin, preferably dissolves said compounds present in the composition according to the invention.

Preferably, solvents and propenetrating agents of avermectin compounds are chosen from propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, polypropylene glycol-15 stearyl ether ("PPG-15 stearyl ether"), octyl dodecanol, ethyl oleate, $C_{12}$-$C_{15}$ alkyl benzoate and mixtures thereof.

More preferably, solvents and propenetrating agents are chosen from a mixture of propylene glycol and oleyl alcohol.

The dermatological or pharmaceutical composition according to the invention preferably comprises from 1 to 10% by weight, preferably from 3 to 7% by weight of solvents and propenetrating agents of avermectin compounds, relative to the total weight of the composition.

The composition according to the invention may comprise one or more surfactants.

Preferably, the surfactants are chosen from non-ionic surfactants.

More preferably the surfactants are chosen from polyoxyethylenated fatty alcohol ethers, sorbitan esters, and mixtures thereof.

As a polyoxyethylenated fatty alcohol ether, mention may be made of ceteareth-20.

As a sorbitan esters, mention may be made of sorbitan monostearate.

The dermatological or pharmaceutical composition according to the invention may comprise from 0.1 to 10% by weight, preferably from 1 to 7% by weight of surfactants, relative to the total weight of the composition.

The composition according to the invention may also comprise at least one gelling agent, preferably at least one aqueous phase gelling agent.

Among the gelling agents which can be used in the composition according to the invention, mention may be made of carboxyvinyl polymers (carbomers) and, by way of non-limiting examples, of carbomer, Carbopol 981, Carbopol ETD 2020, Carbopol 980, Carbopol Ultrez 10 NF and Pemulen TR1, marketed by Lubrizol.

Preferably, the gelling agents are chosen from acrylates/$C_{10\text{-}30}$ alkyl acrylate crosspolymer (Pemulen TR1).

As gelling agent according to the invention, use will preferably be made of carbomers, and preferably Pemulen TR1.

The composition of the invention preferentially contains from 0.01 to 5%, and preferably from 0.1 to 3%, of gelling agents.

Preferably, the gelling agents are in the aqueous phase of the composition.

The aqueous phase of the composition according to the invention comprises water.

The composition according to the invention may also contain inert additives or combinations of these additives, such as flavor enhancers; preservatives; stabilizers; humidity regulators; pH regulators; osmotic pressure modifiers; UV-A and UV-B screening agents; and antioxidants.

Of course, one skilled in this art will take care to choose the optional compound(s) to be added to the composition of the invention in such a way that the advantageous properties intrinsically associated with the present invention are not, or are not substantially, altered by the envisaged addition.

These additives may be present in the composition at from 0.001 to 20% by weight relative to the total weight of the composition.

As described above, the composition according to the invention comprises at least one active phase and at least one aqueous phase.

Preferably, the composition according to the invention is suited for treating the skin and can be in liquid, pasty or solid form, and more particularly in the form of ointments, creams, milks, pomades, powders, impregnated pads, syndets, towelettes, solutions, gels, sprays, foams, suspensions, lotions, sticks, shampoos or washing bases.

It may also be in the form of suspensions of microspheres or nanospheres or of lipid or polymeric vesicles or of polymeric patches and of hydrogels for controlled release.

The composition according to the invention comprises preferably from 5 to 95% of active phase and from 5 to 95% of aqueous phase, more preferably said composition comprises from 5 to 30% of active phase and from 70 to 95% of aqueous phase.

The pH will preferably range from 5.0 to 7.0, more preferably from 6.0 to 6.5.

Verification of the natural pH of the mixture and possible correction with a solution of a neutralizing agent, and also the incorporation of the optional additives, may be carried out, according to their chemical nature, during one of the steps of the method of preparation, described below.

In a preferred embodiment, the composition according to the invention has a viscosity ranging from 1000 to 10000 cP, preferably from 1500 to 5000 cP measured at room temperature using a Brookfield LV.

In a preferred embodiment, the composition according to the invention has a yield stress ranging from 5 Pa to 50 Pa, preferably from 10 to 20 Pa at room temperature using a Malvern rheometer.

In a particular embodiment, the composition according to the invention comprises:
  at least one active phase comprising from 0.01 to 10% by weight, preferably from 0.1 to 5% by weight, relative to the total weight of the composition, of avermectin compounds and from 1 to 10% by weight, preferably from 3 to 7% by weight of solvents and propenetrating agents of avermectin compounds,
  at least one aqueous phase,
  where the composition comprises less than 3% by weight of solid fatty substances.

More preferably in this embodiment, the composition according to the invention comprises:
  at least one active phase comprising from 0.01 to 10% by weight, preferably from 0.1 to 5% by weight, relative to the total weight of the composition, of avermectin compounds and from 1 to 10% by weight, preferably from 3 to 7% by weight of solvents and propenetrating agents of avermectin compounds,
  at least one aqueous phase,
  where the composition comprises less than 3% by weight of solid fatty substance chosen from fatty acids, fatty alcohols, waxes, gums, and mixtures thereof.

According to this embodiment, avermectin compound is preferably ivermectin.

According to this embodiment, the composition preferably comprises at least one gelling agent chosen from acrylates/$C_{10\text{-}30}$ alkyl acrylate crosspolymer.

According to this embodiment, the composition preferably comprises one or more surfactants.

In another particular embodiment, the composition comprises:
  at least one active phase comprising at least one active compound chosen from avermectin compounds,
  at least one aqueous phase,
  at least one solvent and/or propenetrating agent of avermectin compounds.
  where the composition does not comprises stearyl alcohol and cetyl alcohol.

The dermatological or pharmaceutical composition according to the invention is preferably a topical composition.

This composition according to the invention is useful to treat dermatological conditions/afflictions.

In particular, the composition according to the invention is useful for the treatment of rosacea, of common acne, of seborrheic dermatitis, of perioral dermatitis, of acneiform rashes, of transient acantholytic dermatosis, of acne necrotica miliaris and of atopic dermatitis.

More particularly, the dermatological or pharmaceutical composition is used in the treatment of rosacea.

In a particular embodiment, the composition according to the invention is useful in a method for the treatment of rosacea characterized in that the composition is administered topically.

The present invention also features a method for preparing the composition which comprises the following step:

a) mixing avermectin compounds with the other components of the active phase, b) mixing the constituents of the aqueous phase to homogeneity, then c) incorporating the active phase into the aqueous phase so as to form the composition.

In order to illustrate the present invention and the advantages thereof, the following specific examples of compositions comprising ivermectin and the physical and chemical stability thereof are given, it being understood that same are intended only as illustrative and in nowise limitative. In said examples to follow, all parts and percentages are given by weight, unless otherwise indicated.

EXAMPLES

1) Preparation of the Compositions

The comparative composition 1 is formulated according to the following procedure:

In a first beaker, weigh the carbomer (Pemulen TR1) polymer and the purified water, mix at 700 rpm and heat to 65° C. (±2° C.) then weigh the rest of the ingredients of the aqueous phase and mix all the aqueous phase.

In a second beaker, weigh the fatty phase without sorbitan monostearate, dimethicone, propyl parahydroxybenzoate, and heat at 65° C. (±2° C.) then weigh sorbitan monostearate and mix together. Weigh dimethicone and propyl parahydroxybenzoate then mix all the fatty phase.

When the fatty phase and aqueous phase are at 65° C. (±2° C.), introduce the fatty phase into the aqueous phase with Rayneri stirring at 900 rpm, then cool the emulsion.

Allow the emulsion to cool to 50° C. (±2° C.).

In a third beaker, solubilize ivermectin in the active phase at 50° C. (±2° C.) then add this mixture to the preceding obtained emulsion.

Allow the emulsion to cool to 35° C. (±2° C.) then adjust the pH to 6.0 with the sodium hydroxide solution then cool the emulsion to room temperature.

|   | Ingredients | 1 (comp.) % by weight relative to the total weight of the composition |
|---|---|---|
| Fatty phase | Isopropyl palmitate | 4.0 |
|  | Cetyl alcohol | 3.5 |
|  | Stearyl alcohol | 2.5 |
|  | Ceteareth-20 | 3.0 |
|  | Sorbitan monostearate | 2.0 |
|  | Dimethicone | 0.5 |
|  | Propyl parahydroxybenzoate | 0.1 |
| Aqueous phase | Pemulen TR1 | 0.2 |
|  | Glycerin | 4.0 |
|  | Methyl parahydroxybenzoate | 0.2 |
|  | Disodium EDTA | 0.05 |
|  | Citric acid | 0.05 |
|  | Phenoxyethanol | 1.0 |
|  | Purified water | qs 100 |
| Active phase | Ivermectin | 1.0 |
|  | Oleyl alcohol | 2.0 |
|  | Propylene glycol | 2.0 |
|  | 10% sodium hydroxide | qs pH |

The composition 2 according to the invention is formulated according to the following procedure:

In a first beaker, weigh the carbomer polymer (Pemulen TR1) and the purified water, mix at 700 rpm and heat to 65° C. (±2° C.) then weigh the rest of the ingredients of the aqueous phase and mix all the aqueous phase.

In a second beaker, weigh the active phase without sorbitan monostearate, and propyl parahydroxybenzoate, heat at 65° C. (±2° C.), then weigh ivermectin and mix together. Then weigh sorbitan monostearate and mix together. Weigh propyl parahydroxybenzoate then mix all the active phase.

Where the active and aqueous phases are at 65° C. (±2° C.), mix the two phases with Rayneri stirring at 900 rpm until complete homogeneity, and then cool.

Allow the emulsion to cool to 35° C. (±2° C.) then adjust the pH to 6.0 with the sodium hydroxide solution.

|   | Ingredients | 2 (inv.) % by weight relative to the total weight of the composition |
|---|---|---|
| Active phase | Ivermectin | 1.0 |
|  | Ceteareth-20 | 3.0 |
|  | Sorbitan monostearate | 2.0 |
|  | Propyl parahydroxybenzoate | 0.1 |
|  | Propylene glycol | 2.0 |
|  | Oleyl alcohol | 2.0 |
| Aqueous phase | Pemulen TR1 | 0.2 |
|  | Glycerin | 4.0 |
|  | Methyl parahydroxybenzoate | 0.2 |
|  | Disodium EDTA | 0.05 |
|  | Citric acid | 0.05 |
|  | Phenoxyethanol | 1.0 |
|  | Purified water | qs 100 |
|  | 10% sodium hydroxide | qs pH |

2) Physical and Chemical Stability of the Compositions

Physical Characteristics of the Compositions at Room Temperature

| Composition | 1 | 2 |
|---|---|---|
| Macroscopic aspect | white to pale yellowish cream | white lotion (pourable) |
| Microscopic aspect | droplets from 2.5 to 15 μm with presence of refringences | droplets from from 3 to 10 μm with presence of refringences |
| pH | 6.30 | 6.07 |
| Viscosity (cP) | 52267 | 2863 |
| Yield stress (Pa) | 142 | 12 |

-continued

| Composition | 1 | 2 |
|---|---|---|
| Ivermectin titer (%/label claim) | 100.0 | 97.1 |

The viscosity is measured by the use of a Brookfield Viscometer (LV dvII+Small sample adaptator Spindle 34 v=12 rpm for composition 1 and sample adaptator Spindle 28 v=12 rpm for composition 2).

The Yield stress is measured by the use of a Rheometer CV0100 Malvern (Cone Plan CP4° 40 mm) with a controlled stress sweep from 0.03 up to 300 Pa.

The viscosity of the composition 2 according to the invention is quite low. Moreover, the yield stress of the composition 2 is lower than the one of the composition 1. Consequently, the composition 2 according to the invention is pourable.

Physical Stability

The table below represents physical stability of the composition 2 according to the invention at 5° C., room temperature (RT) and 40° C. during three months.

| | 1 month | | | 2 months | | |
|---|---|---|---|---|---|---|
| Composition 2 | 5° C. | RT | 40° C. | 5° C. | RT | 40° C. |
| Macroscopic aspect | No change relative to T0 | | | No change relative to T0 | | |
| Microscopic aspect | No change relative to T0 | | | No change relative to T0 | | |
| pH | 6.15 | 6.11 | 6.07 | 6.07 | 6.01 | 5.99 |

| | 3 months | | |
|---|---|---|---|
| Composition 2 | 5° C. | RT | 40° C. |
| Macroscopic aspect | No change relative to T0 | | |
| Microscopic aspect | No change relative to T0 | | |
| pH | 6.14 | 6.04 | 6.10 |

The composition 2 according to the invention is physically stable three months at 5° C., room temperature (RT) and 40° C.

Chemical Stability

The table below represents chemical stability of the composition 2 according to the invention at room temperature (RT) and 40° C. during 3 months.

| Ivermectin titer (%/T0) | | Composition 2 |
|---|---|---|
| 2 months | RT | 99.6 (CV 0.6%) |
| | 40° C. | 98.8 (CV 0.1%) |
| 3 months | RT | 100.4 (CV 0.0%) |
| | 40° C. | 98.8 (CV 0.1%) |

CV: coefficient of variation

Composition 2 is chemically stable three months at room temperature and 40° C.

The invention claimed is:

1. A dermatological or pharmaceutical composition, comprising:
   (a) 70 to 95% by weight, relative to the total weight of the composition, of at least one aqueous phase; and
   (b) 5 to 30% by weight, relative to the total weight of the composition, of at least one active phase comprising at least one avermectin compound and at least one solvent and/or propenetrating agent of avermectin compounds, wherein the composition comprises less than 3% by weight of solid fatty substances at room temperature and at atmospheric pressure, relative to the total weight of the composition.

2. The dermatological or pharmaceutical composition according to claim 1, wherein solid fatty substances are selected from fatty acids, fatty alcohols, waxes, gums, and mixtures thereof.

3. The dermatological or pharmaceutical composition according to claim 1, wherein the composition does not comprise stearyl alcohol and cetyl alcohol.

4. The dermatological or pharmaceutical composition according to claim 3, wherein the composition does not comprise any solid fatty substance.

5. The dermatological or pharmaceutical composition according to claim 1, wherein the avermectin compound is selected from ivermectin, invermectin, avermectin, abamectin, doramectin, eprinomectin and selamectin.

6. The dermatological or pharmaceutical composition according to claim 5, wherein the avermectin compound is ivermectin.

7. The dermatological or pharmaceutical composition according to claim 1, comprising from 0.01 to 10% by weight, of the at least one avermectin compound, relative to the total weight of the composition.

8. The dermatological or pharmaceutical composition according to claim 7, comprising from 0.1 to 5% by weight, of the at least one avermectin compound, relative to the total weight of the composition.

9. The dermatological or pharmaceutical composition according to claim 1, wherein solvents and propenetrating agents of avermectin compounds are selected from propylene glycol, ethanol, isopropanol, butanol, N-methyl-2-pyrrolidone, dimethylsulfoxyde, polysorbate 80, poloxamer 124, phenoxyethanol, oleyl alcohol, isostearic acid, diisopropyl adipate, polypropylene glycol-15 stearyl ether ("PPG-15 stearyl ether"), octyl dodecanol, ethyl oleate, C12-C15 alkyl benzoate and mixtures thereof.

10. The dermatological or pharmaceutical composition according to claim 1, comprising 1 to 10% by weight of solvents and propenetrating agents of avermectin compounds, relative to the total weight of the composition.

11. The dermatological or pharmaceutical composition according to claim 1, comprising 3 to 7% by weight of solvents and propenetrating agents of avermectin compounds, relative to the total weight of the composition.

12. The dermatological or pharmaceutical composition according to claim 1, further comprising one or more surfactants.

13. The dermatological or pharmaceutical composition as defined in claim 12, wherein the surfactants are selected from non-ionic surfactants.

14. The dermatological or pharmaceutical composition as defined in claim 12, wherein the surfactants are selected from polyoxyethylenated fatty alcohol ethers, sorbitan esters, and mixtures thereof.

15. A method of treating rosacea, common acne, seborrheic dermatitis, perioral dermatitis, acneiform rashes, transient acantholytic dermatosis, acne necrotica miliaris and/or atopic dermatitis, comprising administering the dermatological or pharmaceutical composition according to claim 1.

16. The method according to claim 15, for the treatment of rosacea.

17. The method according to claim 16, wherein the dermatological or pharmaceutical composition is administered topically.

18. A method for preparing the composition according to claim 1, comprising:
  (a) mixing the at least one avermectin compound with the other components of the active phase, wherein the active phase is present at a concentration of 5 to 30% by weight, relative to the total weight of the composition;
  (b) mixing the constituents of the aqueous phase to homogeneity, wherein the aqueous phase is present at a concentration of 70 to 95% by weight, relative to the total weight of the composition; and then
  (c) incorporating the active phase into the aqueous phase so as to form the composition.

19. The composition of claim 1, wherein the viscosity of the composition is from about 1000 cP to 10000 cP at room temperature.

20. The composition of claim 1, wherein the viscosity of the composition is from about 1500 cP to 5000 cP at room temperature.

21. The composition of claim 1, wherein the yield stress of the composition is from about 5 Pa to 50 Pa at room temperature.

22. The composition of claim 1, wherein the yield stress of the composition is from about 10 Pa to 20 Pa at room temperature.

* * * * *